United States Patent
Jones et al.

[11] Patent Number: 5,766,202
[45] Date of Patent: Jun. 16, 1998

[54] WIRE-GUIDED ESOPHAGAEL BOUGIE

[75] Inventors: Richard G. Jones, West Chester, Pa.; Jeff Miner, Sanford, Mich.

[73] Assignee: Pilling Weck Incorporated, Fort Washington, Pa.

[21] Appl. No.: 786,785

[22] Filed: Jan. 21, 1997

[51] Int. Cl.⁶ .................................................. A61M 25/00
[52] U.S. Cl. .......................... 606/196; 604/270; 604/280
[58] Field of Search .................... 604/29, 54, 94, 604/104, 170, 270, 264, 280; 606/191, 196

[56] References Cited

U.S. PATENT DOCUMENTS

| | | |
|---|---|---|
| 4,516,970 | 5/1985 | Kaufman et al. |
| 4,631,054 | 12/1986 | Kim ............................. 604/270 |
| 4,726,373 | 2/1988 | Greengrass . |
| 4,874,365 | 10/1989 | Frederick et al. . |
| 5,017,193 | 5/1991 | Fields . |
| 5,078,701 | 1/1992 | Grassi et al. ................. 604/270 |
| 5,366,471 | 11/1994 | Jones et al. . |
| 5,599,322 | 2/1997 | Quinn ............................ 604/270 |

FOREIGN PATENT DOCUMENTS

| | | |
|---|---|---|
| 811717 | 8/1951 | Germany . |
| WO 84/04462 | 11/1984 | WIPO . |

OTHER PUBLICATIONS

1993 Pilling Catalog pp. 127 & 543 describing Hurst and Maloney bougies.

Esophageal Dilation: Instruments and Techniques, May 1988, pp. 473–475.

*Primary Examiner*—Michael Powell Buiz
*Assistant Examiner*—William W. Lewis
*Attorney, Agent, or Firm*—Howson & Howson

[57] ABSTRACT

A wire-guided esophageal bougie comprises a PTFE-lined, silicone rubber tube with a tapered, silicone rubber dilator on its distal end, the dilator being more flexible than the PTFE-lined tube. Radiopaque material throughout the length of the tube renders it fluoroscopically visible in the esophagus while a radiopaque ring in the dilator fluoroscopically locates the position of the dilator relative to a stricture.

9 Claims, 1 Drawing Sheet

WIRE-GUIDED ESOPHAGAEL BOUGIE

BRIEF SUMMARY OF THE INVENTION

This invention relates generally to bougies; and, more particularly, to a novel and improved wire-guided esophageal bougie for treating disorders associated with strictures of the esophagus.

Dysphagia or difficulty in passing food down the esophagus is a common symptom of esophageal disorders. These disorders are usually produced by a stricture in the esophagus or by an impairment of peristalsis and lower esophageal sphincter relaxation. After an initial esophagoscopic assessment, the stenosis is dilated by means of an esophageal bougie to assist in diagnostic inspection and treatment.

Several types of prior art esophageal bougies, for example, are discussed in U.S. Pat. No. 5,366,471 to Richard G. Jones, et al. One wire-guided type, in particular, is a bougie of choice for use in certain malignant sphincters and for extremely tight fibrotic strictures 1.2 cm or less in diameter. The wire-guided bougie may be used, in addition to other types of bougies, for other strictures. Its entire length is constructed of a hollow tube of rubber, silicone rubber or a pliable plastic of sufficient flexibility to negotiate tight or tortuous paths but without risk of misdirection or kinking of the guide wire. The insertion or distal part of the tube gradually tapers from a maximum width required for dilating a stricture down to a rounded tip. The hollow center of the bougie enables it to be passed along a guide wire previously inserted in the esophagus. The guide wire may be coated with a silicone or PTFE (polytetrafluoroethylene) for reducing friction between it and the bougie to enhance tactile sensations as the surgeon carefully feeds the dilator through a stricture. The tapered end may be radiopaque, particularly in the region of maximum width, to permit fluoroscopic monitoring.

Great care is required in feeding the bougie through a strictured region especially where the esophageal tissue may have become soft, as a misdirection or false passage could perforate the esophagus and force the dilator into the mediastinum, into one or the other pleural cavity, or even into the pericardium. Such a misdirection is also critical where symptoms of a stricture may be produced by an aneurism of some part of the aorta pressing upon the esophagus.

SUMMARY OF THE INVENTION

Accordingly, it is an object of the present invention to provide a wire-guided esophageal bougie which can be easily passed through the esophageal lumen onto a guide wire previously placed in the esophagus, and which provides an enhanced tactile sensation to the surgeon.

Another object is to provide a wire-guided bougie in which a dilator at the distal end is more flexible relative to the remaining proximal portion of the bougie for reducing the risk of misdirection or kinking of the guide wire as the bougie is inserted through a tight or tortuous path in the esophagus.

Still another object of the invention is to provide a simple mechanical instrument which is clearly visible and easy to manipulate under fluoroscopy.

These and other objects are accomplished according to the invention by a wire-guided esophageal bougie comprising an elongate tube and a tapered dilator with a central bore coaxially extending from the distal end. A smooth pliable plastic liner, longitudinally disposed within the entire length of the tube, projects into an adjoining portion of the dilator and communicates with the bore of the dilator, allowing the bougie to be passed over a guide wire previously inserted into the esophagus. The entire length of the tube is composed of a flexible material such as silicone rubber, and contains a radiopaque material for rendering an image of the tube visible under fluoroscopic exposure. The dilator is also made of similar flexible material but with the radiopaque material restricted to a band around the location of maximum width of the dilator for providing a visual "beacon" showing its precise location relative to a stricture. The smooth sleeve reduces the sliding friction between the bougie and the guide wire, thereby enhancing the tactility as the bougie to the surgeon as the bougie is pushed along the guide wire and into the esophagus. The sleeve also imparts sufficient stiffness to the tube to minimize the risk of kinking of the guide wire as the bougie is inserted. However, the tapered dilator remains flexible enough to negotiate tight and tortuous paths and to lead the bougie through the strictured part without risk of a false passage.

Other objects, novel features and advantages of the invention will become apparent from the following detailed description when read in conjunction with the drawings.

DETAILED DESCRIPTION

Figure 1:
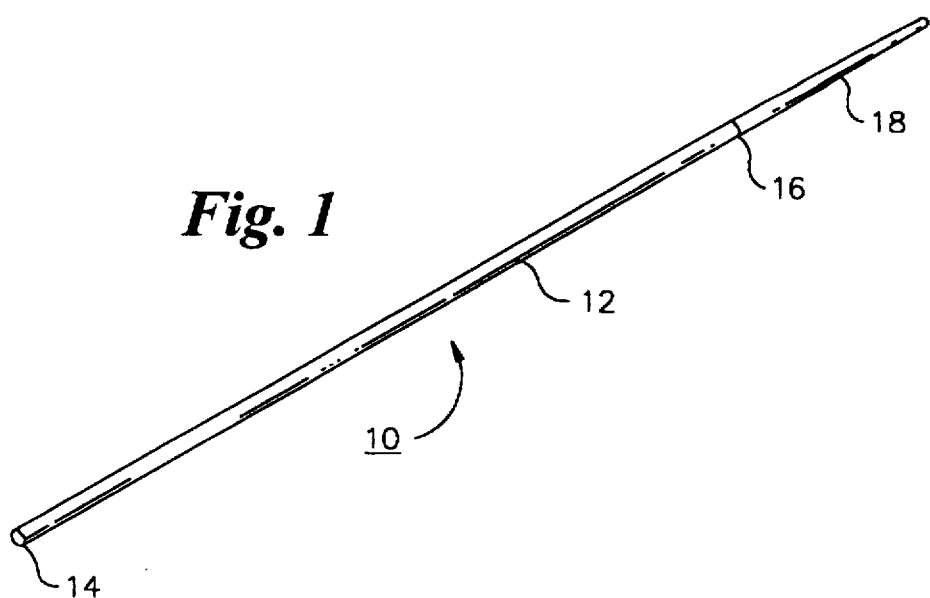
FIG. 1 is a perspective view of a wire-guided esophageal bougie according to the invention.
Figure 2:
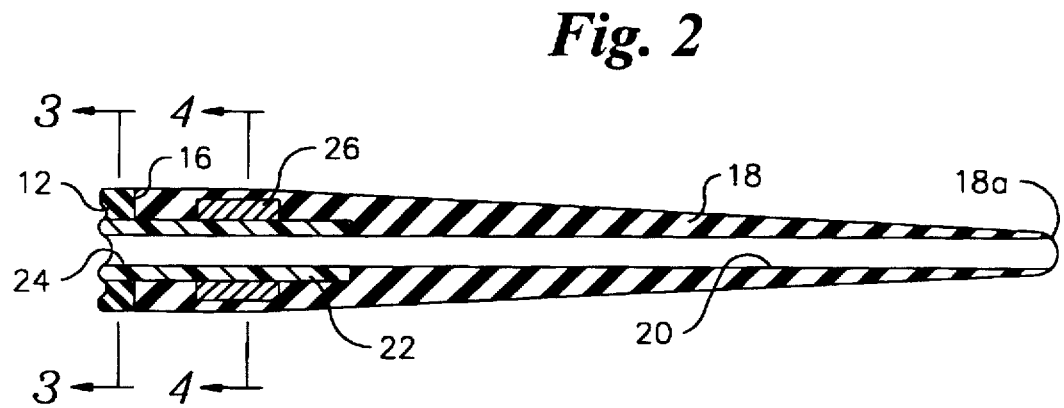
FIG. 2 is a view in longitudinal cross-section of the distal end of the bougie in FIG. 1.
Figure 3:
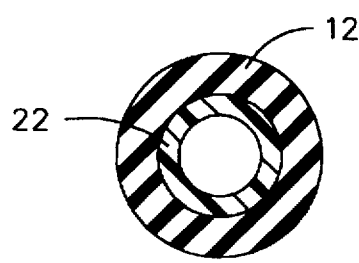
FIG. 3 is a view in radial cross-section of the bougie taken on plane 3—3 of FIG. 2.
Figure 4:
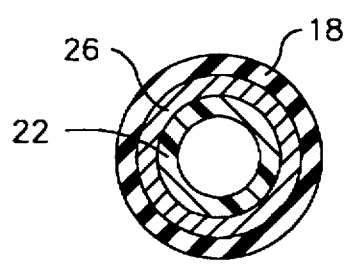
FIG. 4 is a view in radial section of the bougie taken on plane 4—4 of FIG. 2.

Referring now to the drawings, wherein like reference characters denote like or corresponding parts throughout the several views, FIGS. 1 and 2 show a wire-guided esophageal bougie 10 according to the invention comprising a flexible tube 12 of constant cross section between a proximal end 14 and a distal end 16. An elongate dilator 18, coaxially extending from distal end 16, includes a central bore 20 along its entire length sized to receive a guide wire (not shown) so that the dilator can slide along the guide wire. The outer surface of dilator 18 is smoothly aligned with the outer surface of tube 12 at a juncture, and gradually tapers to form a relatively flexible end portion at a rounded tip 18a for ease of insertion via the pharynx into the esophagus. A sleeve 22, lining the interior of tube 12 and extending from distal end 16 into dilator 18. The sleeve 22 provides support for the proximal end of the dilator and holds the dilator securely to tube 12. The central passage 24 of sleeve 22 is sized to pass the guide wire. Its diameter is preferably the same as the diameter of bore 20 in the dilator. The distal end of passage 24 is aligned with the proximal end of bore 20 so that the passage 24 of the sleeve and the bore 20 of the dilator communicate with each other to form a continuous, smooth passage along the length of bougie 10.

Tube 12 is preferably a flexible silicone composition, such as silicone rubber, which meets USP Class IV specifications, and includes a radiopaque material such as Tungsten particles dispersed along its entire length to allow the bougie 10 to be observed fluoroscopically in the esophagus.

Dilator 18, on the other hand, is made of a similar silicone composition, except the radiopaque material is omitted.

Instead a radiopaque ring 26 is provided at or near the location of maximum width of dilator 18 to enable the location of the dilator in the esophagus to be monitored precisely relative to the stricture being treated.

Sleeve 22 is fabricated of a low-friction pliable plastics material, preferably a synthetic resin such as PTFE, which will lend stiffness to tube 12 relative to dilator 18 and thereby minimize the risk of kinking of the wire as the wire is inserted into the bougie. Dilator 18 remains flexible enough to bend and lead the bougie through tight turns without false direction, particularly in the area of the cricopharyngeus muscle structure and the stricture. Being made of a low friction plastics material, sleeve 22 also offers the surgeon greater tactility at the proximal end 14 of the bougie as it is pushed through the esophagus.

Typical approximate dimensions of bougie 10 according to the invention are an overall length of about 75 cm overall length including 15 cm for dilator 18. Dilators may be provided in different sizes. For example, the maximum width (diameter in the case of a circular cross section) may range from about 5.4 mm to 20 mm in a typical set of dilators. The diameter at the location at which the rounded tip meets the tapered part of the dilator is typically about 4.7 mm.

Some of the many advantages and novel features of the invention should now be readily apparent. For example, a wire-guided esophageal bougie is provided which will slide substantially friction-free onto a guide wire which has been previously introduced into the esophagus. By virtue of the greater flexibility of the tapered dilator, especially nearer its tip, relative to the tube, there is little risk of false direction or kinking of the wire as the bougie is pushed through tight or tortuous paths. The bougie can be observed by fluoroscopy over its entire length while the position of the dilator relative to the stricture being treated can be precisely monitored.

It will be understood, of course, that various changes in the details, materials, steps and arrangement of parts, which have been herein described and illustrated in order to explain the nature of the invention, may be made by those skilled in the art within the principal and scope of the invention as expressed in the appended claims.

We claim:

1. A wire-guided esophageal bougie for treating disorders associated with a stricture of the esophagus, comprising, in combination:
   a flexible tube having a distal end and a proximal end and an interior wall extending from the distal end to the proximal end;
   an elongate dilator also having distal and proximal ends, the dilator being fixed at its proximal end to the distal end of the tube and tapered in the distal direction to a rounded tip, and having a central bore extending from its distal end to its proximal end; and
   a pliable liner fixed to the interior wall of the tube and having a central bore communicating with the bore of the dilator to form a continuous passage through which a guide wire placed in the esophagus extends when the bougie is in use,
   in which the pliable liner comprises a low friction plastics material for enhancing tactility when the bougie is in use.

2. A bougie according to claim 1 in which a portion of the pliable liner extends into the elongate dilator.

3. A bougie according to claim 1 in which the bores of the pliable liner and elongate dilator are of the same diameter.

4. A bougie according to claim 1 wherein the flexibilities of the flexible tube and the pliable liner are such that the flexible tube and pliable liner in combination form a tubular structure having a flexibility less than the flexibility of the elongate dilator along substantially the entire length of the elongate dilator, whereby kinking of the guide wire is avoided, and the bougie is able to negotiate tight and tortuous paths without misdirection.

5. A bougie according to claim 1 wherein the flexible tube and the elongate dilator comprise a silicone rubber.

6. A bougie according to claim 1 including a radiopaque material uniformly distributed within the tube along its entire length, for enabling fluoroscopic imaging.

7. A bougie according to claim 1 wherein the low friction plastics material is PTFE.

8. A wire-guided esophageal bougie for treating disorders associated with a stricture of the esophagus, comprising, in combination:
   a flexible tube having a distal end and a proximal end and an interior wall extending from the distal end to the proximal end;
   an elongate dilator also having distal and proximal ends, the elongate dilator having a location of maximum width adjacent to its proximal end, being fixed at its proximal end to the distal end of the tube, and being tapered in the distal direction to a rounded tip, and having a central bore extending from its distal end to its proximal end; and
   a pliable liner fixed to the interior wall of the tube and having a central bore communicating with the bore of the elongate dilator to form a continuous passage through which a guide wire placed in the esophagus extends when the bougie is in use;
   wherein the elongate dilator includes a radiopaque ring substantially at said location of maximum width for locating the dilator relative to a stricture of the esophagus.

9. A wire-guided esophageal bougie for treating disorders associated with a stricture of the esophagus, comprising, in combination:
   a silicone rubber tube having a distal end and a proximal end, and an interior wall extending from the distal end to the proximal end;
   a silicone rubber dilator also having distal and proximal ends, the silicone rubber dilator being fixed at its proximal end to the distal end of the silicone rubber tube and tapered in the distal direction to a rounded tip, and having a central bore extending from its distal end to its proximal end; and
   a pliable liner of plastics material, fixed to the interior wall of the silicone rubber tube and forming a tubular structure, the pliable liner having a portion extending into the silicone rubber dilator, the pliable liner having a central bore communicating with the bore of the silicone rubber dilator to form a continuous passage through which a guide wire placed in the esophagus extends when the bougie is in use;
   the flexibilities of the silicone rubber tube and the pliable liner being such that the silicone rubber dilator, along substantially its entire length, has a flexibility greater than the flexibility of the tubular structure, whereby the wire-guided bougie is able to negotiate tight and tortuous paths without misdirection, and kinking of the guide wire is avoided.

* * * * *